（12）United States Patent
Takahashi et al.

(10) Patent No.: US 7,847,549 B2
(45) Date of Patent: Dec. 7, 2010

(54) MAGNETIC RESONANCE IMAGING APPARATUS

(75) Inventors: Tetsuhiko Takahashi, Tokyo (JP); Takayuki Abe, Tokyo (JP); Hisako Nagao, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 380 days.

(21) Appl. No.: 12/159,177

(22) PCT Filed: Dec. 26, 2006

(86) PCT No.: PCT/JP2006/325933

§ 371 (c)(1),
(2), (4) Date: Jun. 25, 2008

(87) PCT Pub. No.: WO2007/077832

PCT Pub. Date: Jul. 12, 2007

(65) Prior Publication Data

US 2010/0219828 A1    Sep. 2, 2010

(30) Foreign Application Priority Data

Jan. 5, 2006    (JP) ............................. 2006-000652

(51) Int. Cl.
*G01V 3/00* (2006.01)
(52) U.S. Cl. .................................................. 324/307
(58) Field of Classification Search ......... 324/300–322; 600/410–435
See application file for complete search history.

(56) References Cited

U.S. PATENT DOCUMENTS

| 2003/0216637 | A1 | 11/2003 | Ho et al. |
| 2005/0171423 | A1 | 8/2005 | Ho et al. |
| 2005/0285595 | A1* | 12/2005 | Green et al. ................ 324/307 |

FOREIGN PATENT DOCUMENTS

| JP | 11-276454 | 10/1999 |
| WO | WO02/04970 A1 | 1/2002 |

* cited by examiner

*Primary Examiner*—Melissa J Koval
*Assistant Examiner*—Dixomara Vargas
(74) *Attorney, Agent, or Firm*—Cooper & Dunham LLP

(57) ABSTRACT

A magnetic resonance imaging apparatus comprises object placing means for placing an object in an imaging space, translating means for translating the object in a given direction by translating the object placing means in the given direction continuously or step-wise, magnetic field generating means for exciting the desired region of the object by generating a static magnetic field, a gradient magnetic field in the imaging space, and a high-frequency magnetic field in the imaging space, signal detecting means for detecting a magnetic resonance signal from the object, and control unit for controlling the translating means, magnetic field generating means and the signal detecting means, and translating the object continuously or stepwise to a predetermined position at a predetermined speed so as to capture a magnetic resonance image of the object.

The magnetic resonance imaging apparatus further comprises translation error detecting means for detecting an error of the position or the set value of the speed, and correcting means for correcting the error detected by the positional error detecting means.

20 Claims, 14 Drawing Sheets

FIG.7
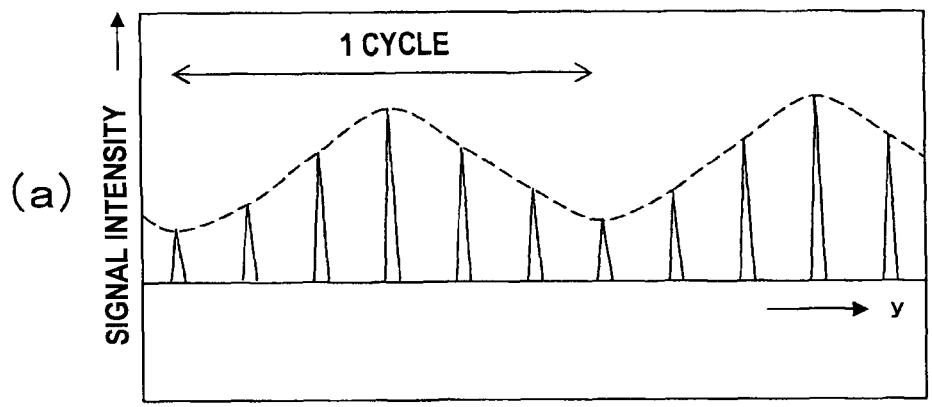
(a)
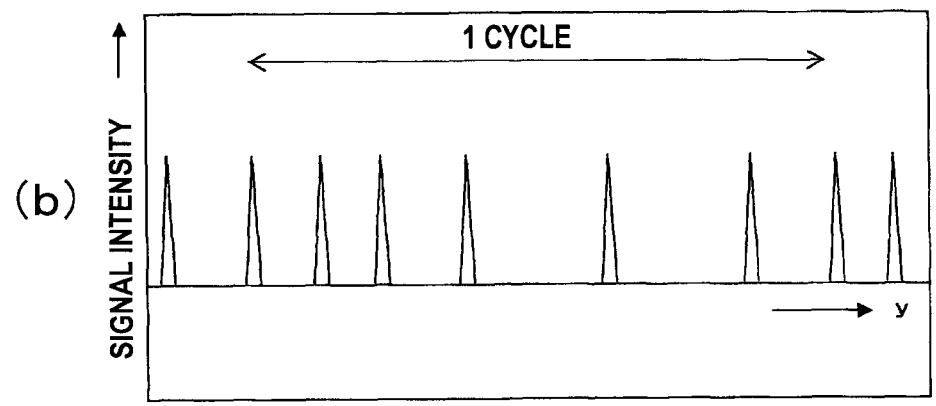
(b)
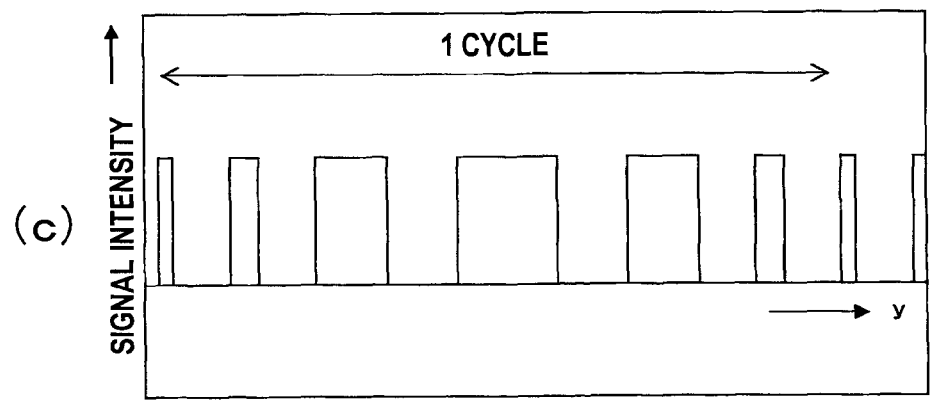
(c)

FIG.9
(a)
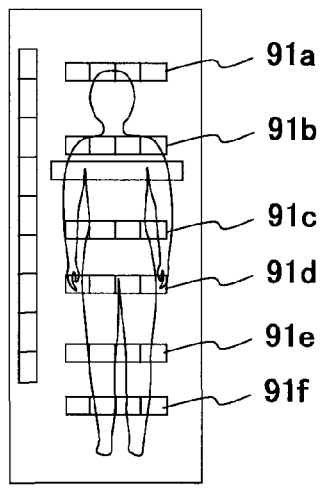
91a
91b
91c
91d
91e
91f
(b)
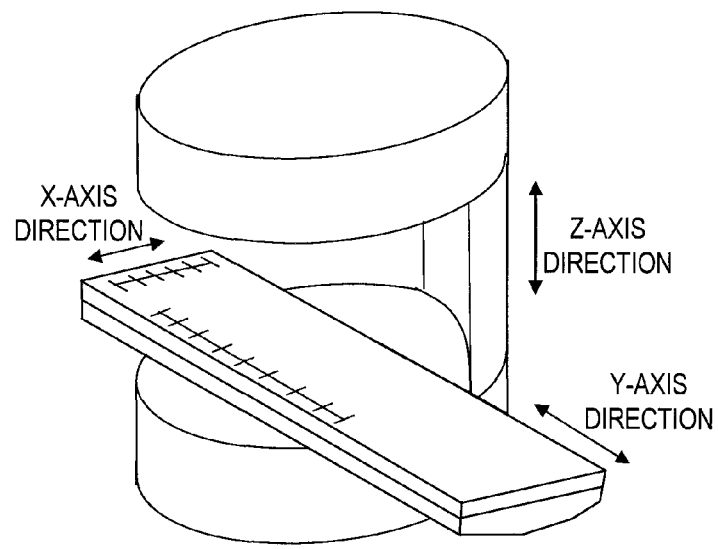
(c)
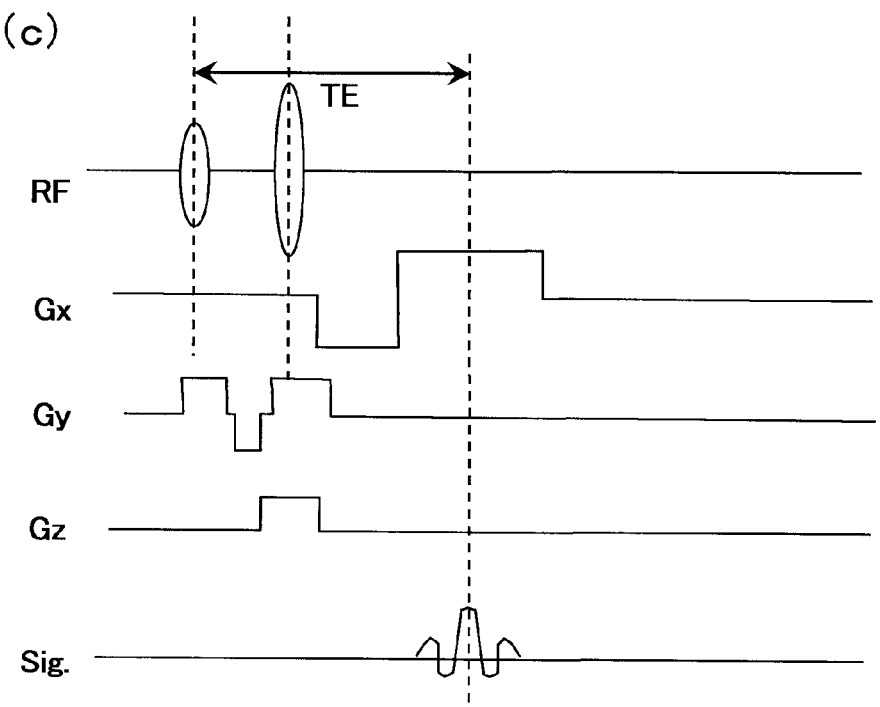

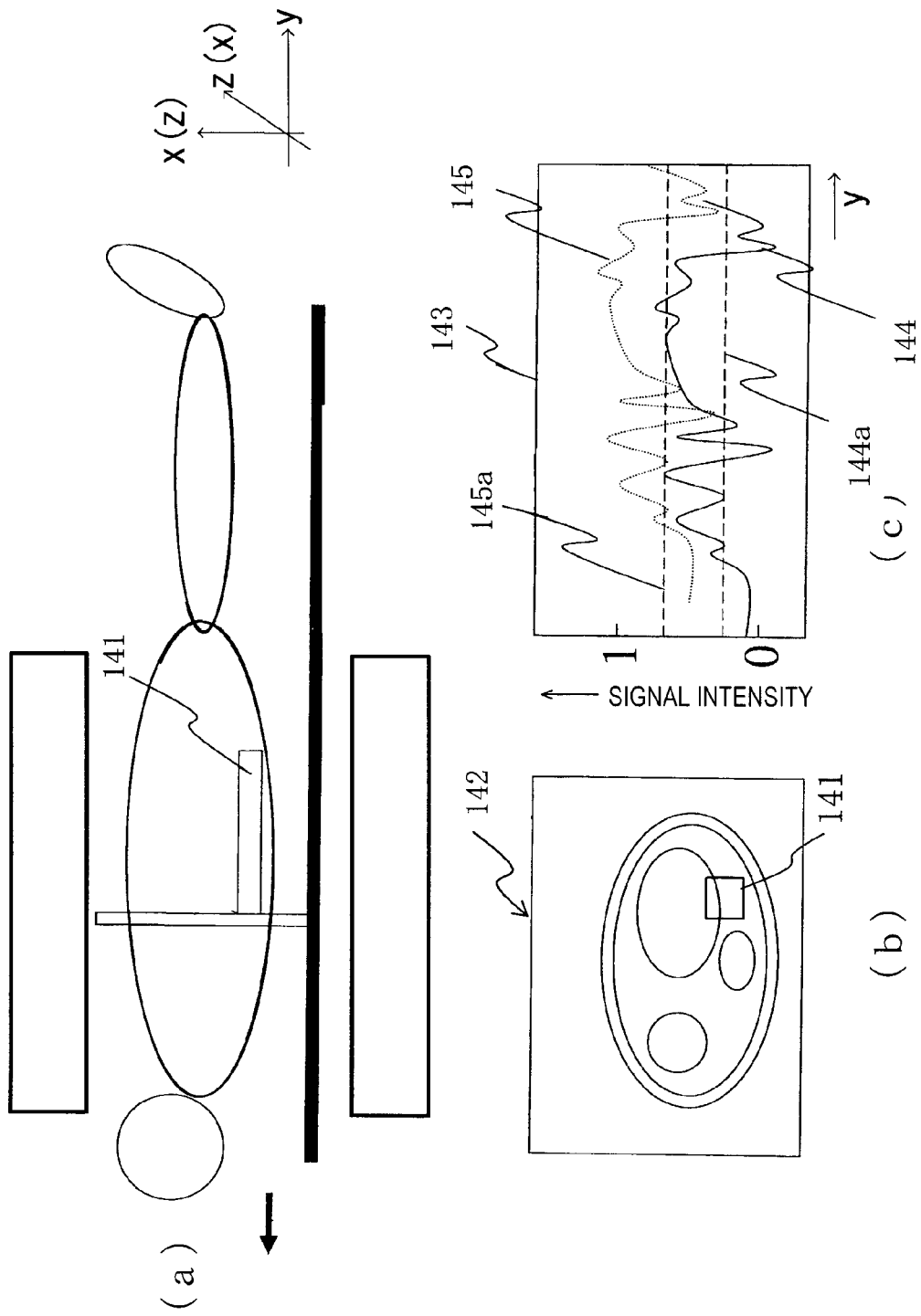

MAGNETIC RESONANCE IMAGING APPARATUS

TECHNICAL FIELD

The present invention relates to a magnetic resonance imaging apparatus (hereinafter referred to as MRI apparatus), in particular to an image quality improvement technique in a method for imaging a wide range of the region of an object to be examined while translating a table.

BACKGROUND ART

An MRI apparatus is for acquiring a magnetic resonance image (hereinafter referred to as an MR image) which represents the physical description of the object, when electromagnetic waves are irradiated to an object placed in a homogeneous static magnetic field, by detecting a nuclear magnetic resonance signal (hereinafter referred to as NMR signal) from the object using nuclear magnetic resonance (hereinafter referred to as NMR) phenomenon being generated in atomic nuclei of atomy by which the object is formed, and constructing an image using the NMR signals.

In MRI, a technique is known for imaging a wide range or a whole body of an object while translating a table on which the object is placed in a gantry of an MRI apparatus. In such technique, there are two ways for translating the table. One is the multi-station imaging method for dividing a wide range or a whole body of the object into a plurality of blocks, and imaging each block while translating the table step-wise (for example, refer to Patent Document 1). The other method is the moving-table imaging method for imaging a wide range or a whole body of the object while continuously moving the table (for example, refer to Patent Document 2).

Patent Document 1: U.S. Pat. No. 6,311,085
Patent Document 2: JP-A-2004-611

However, after reviewing the above-mentioned conventional techniques, the present inventors found the following problems.

In the above-mentioned conventional technique, in the case of imaging while translating the table continuously or step-wise and translation accuracy is low, since the image of the object is reconstructed by performing Fourier transformation etc. on the signal data obtained in the position on the object that is different from the original position meant to be imaged, the moving-table imaging method has a problem with motion artifacts being generated over the entire image, and the multi-station imaging method has a problem with a gap being generated between the adjacent stations (spatial regions which could not acquire a magnetic resonance signal) when excess amount of table translation is performed. While a technique is disclosed in Patent Document 3 for using navigator echoes to correct artifacts of the images obtained while the object is being translated, a technique related to the method on how to detect low-level of table movement accuracy (error in the case that the obtained positional data of the object is different from the original position meant to be obtained) in order to reduce deterioration of image quality is not disclosed.

Patent Document 3: JP-A-H8-173396

DISCLOSURE OF THE INVENTION

The object of the present invention is to reduce deterioration of image quality due to low level of the table movement accuracy in the MRI apparatus or method for acquiring MR images while translating the table on which the object is placed continuously or step-wise.

The present invention provides an MRI apparatus comprising:

object placing means for placing an object to be examined in an imaging space;

translating means for translating the object by translating the object placing means in a given direction continuously or step-wise, magnetic field generating means to be placed around the imaging space, and for exciting the desired region of the object by generating a static magnetic field, a gradient magnetic field and high-frequency magnetic field in the imaging space;

signal detecting means to be placed around the imaging space, and for detecting a magnetic resonance signal generated from the object;

signal processing means for processing the magnetic resonance signal detected by the signal detecting means and constructing a magnetic resonance image of the object; and control unit for controlling the translating means, the magnetic field generating means, the signal detecting means and the signal processing means, and for controlling to obtain a magnetic resonance image of the object while translating the object continuously or step-wise to a predetermined position at a predetermined speed, characterized in further comprising:

translation error detecting means for detecting an error with respect to the set value of the position or the speed; and correcting means for correcting the error detected by the positional error detecting means.

BRIEF DESCRIPTION OF THE DIAGRAMS

Figure 6:
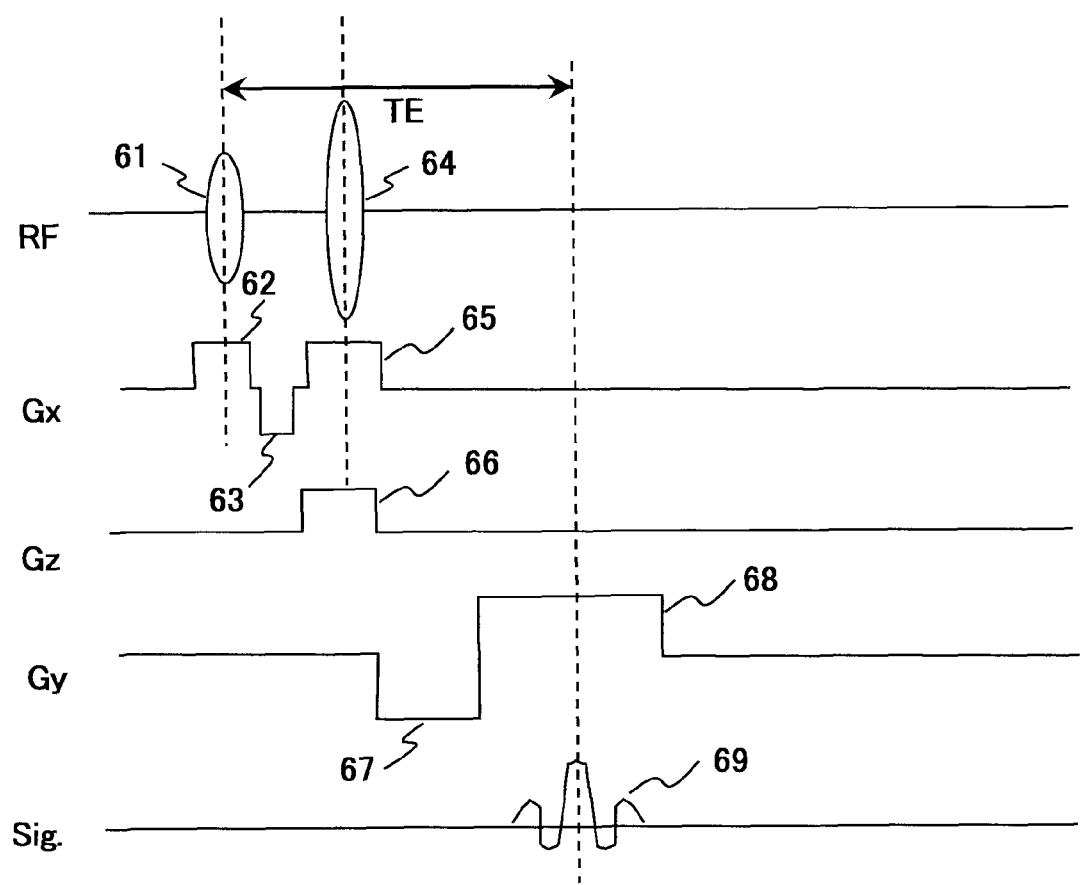

FIG. 6 explains a navigator sequence.

FIG. 7 is for explaining a scale 44 in which the signal intensity (amplitude) of the obtained one-dimensional profile changes periodically.

Figure 8:
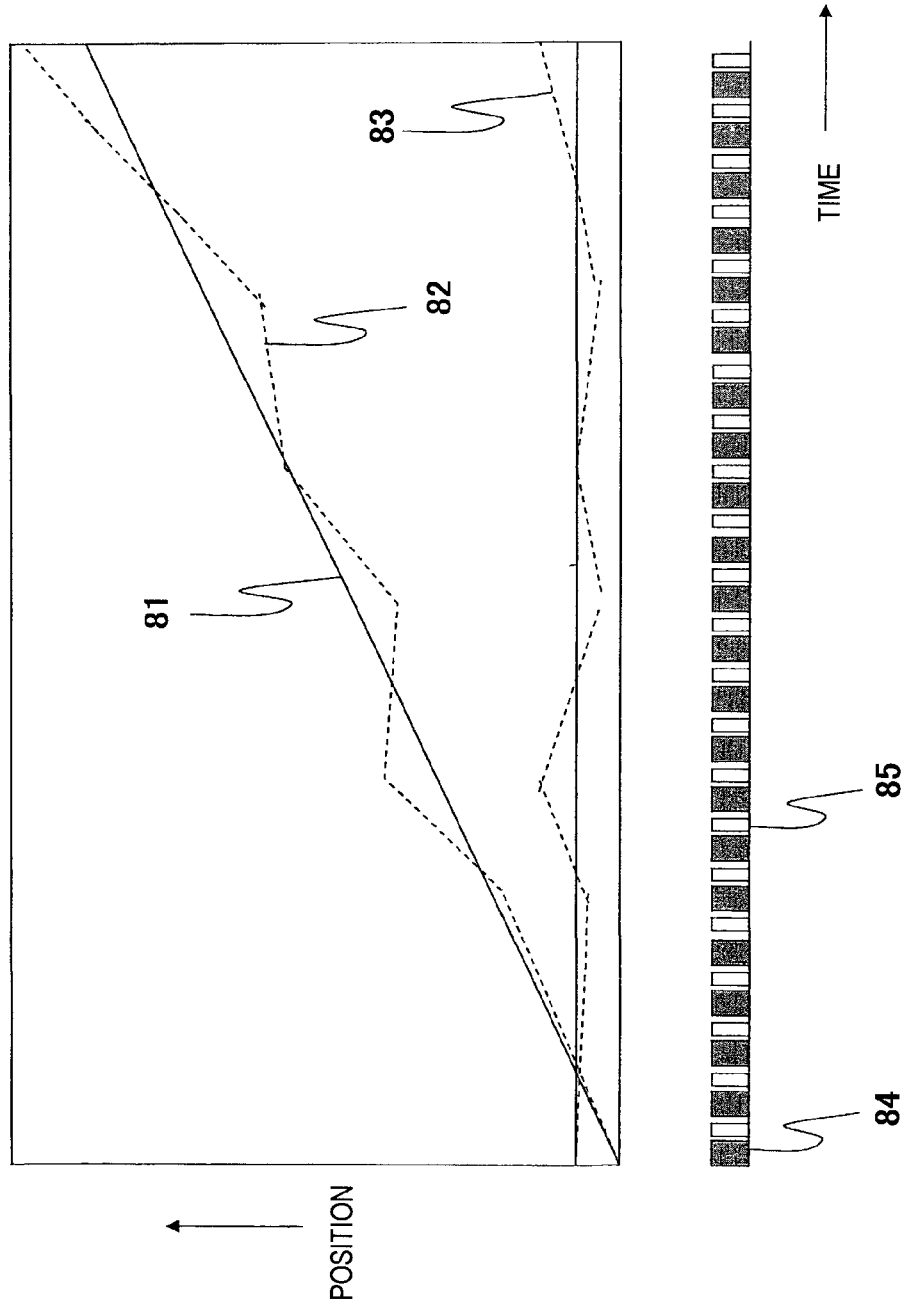

FIG. 8 shows an example of the relationship between the position of the table 37 obtained by a navigator echo in embodiment 1 and the position of the table when there is no error in table translation, which is represented in a graph form using the coordinate system of the apparatus.

FIG. 9 is an explanatory view of the case in which a plurality of scales whose longitudinal direction thereof are parallel to the x-direction, and are disposed in the table translating direction (y-direction) at predetermined interval.

Figure 10:
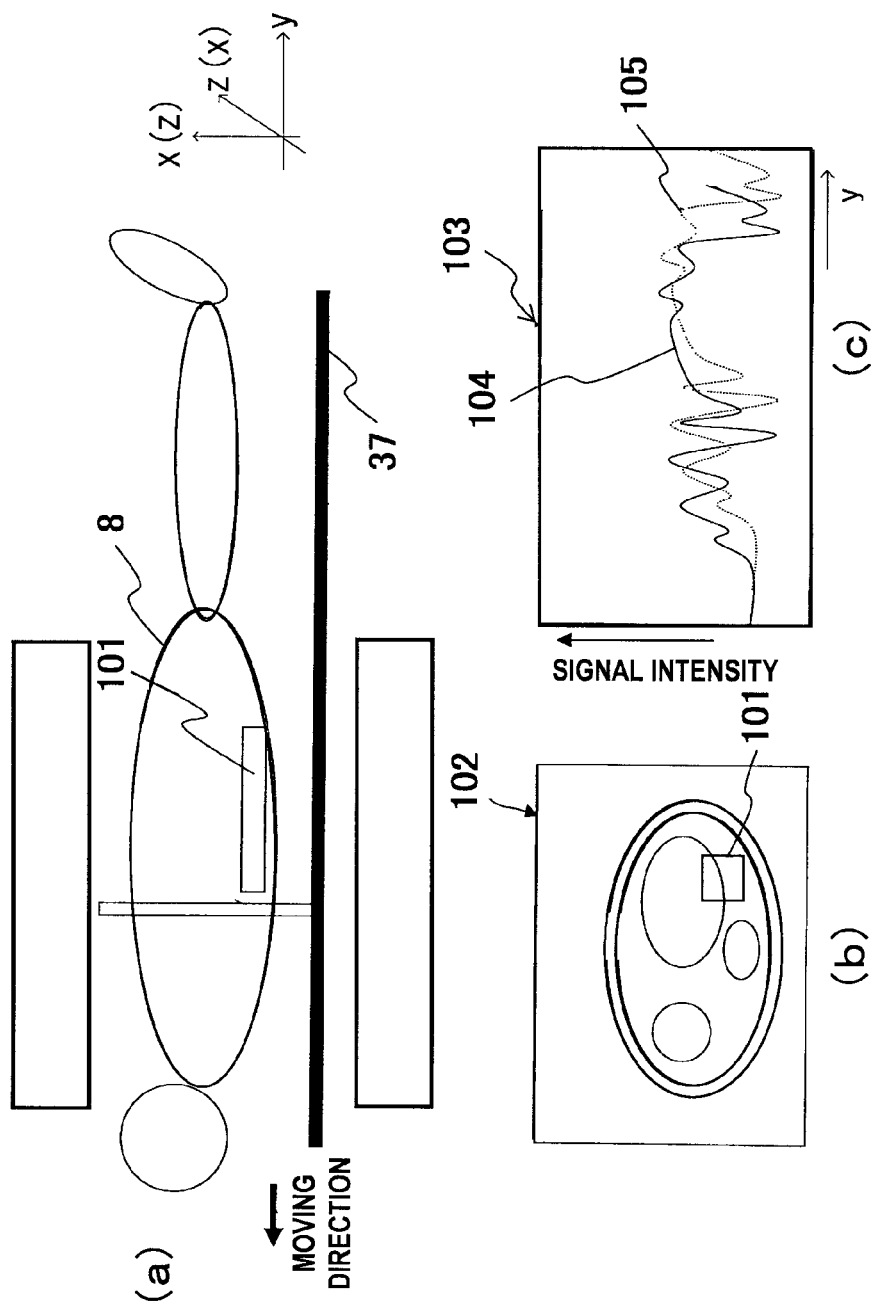

FIG. 10 is an explanatory diagram of the MRI apparatus in embodiment 2.

Figure 11:
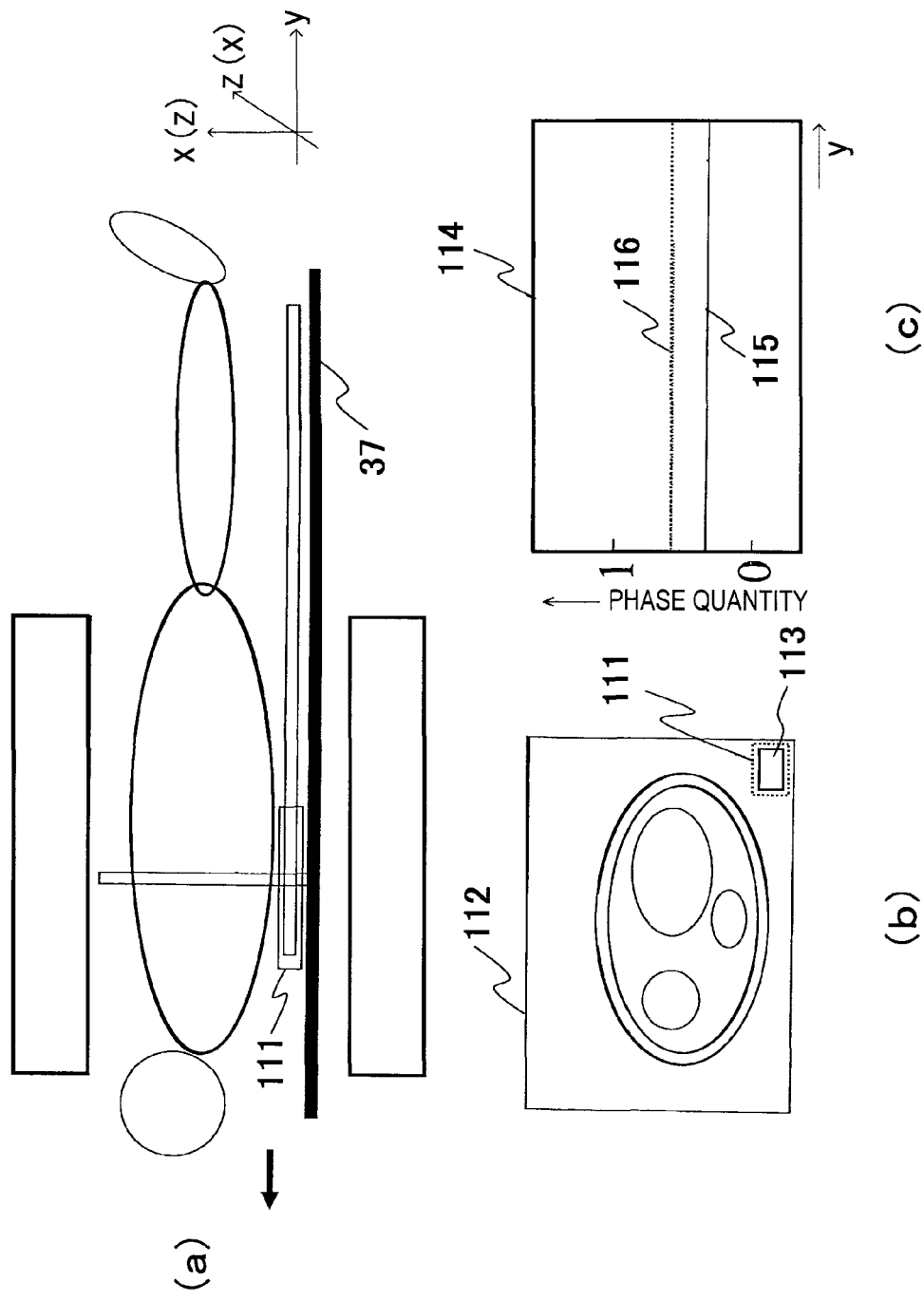

FIG. 11 is an explanatory diagram of the MRI apparatus in embodiment 3.

Figure 12:
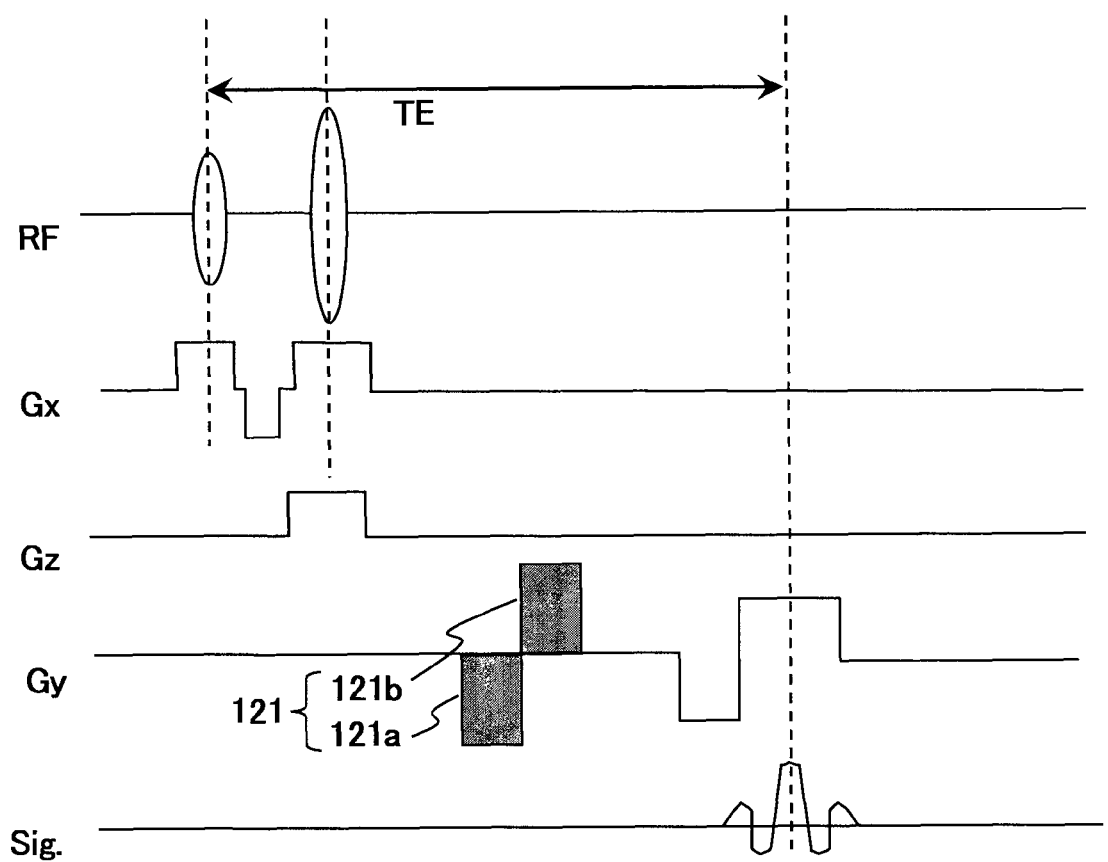

FIG. 12 is for explaining the sequence diagram in embodiment 3.

Figure 13:
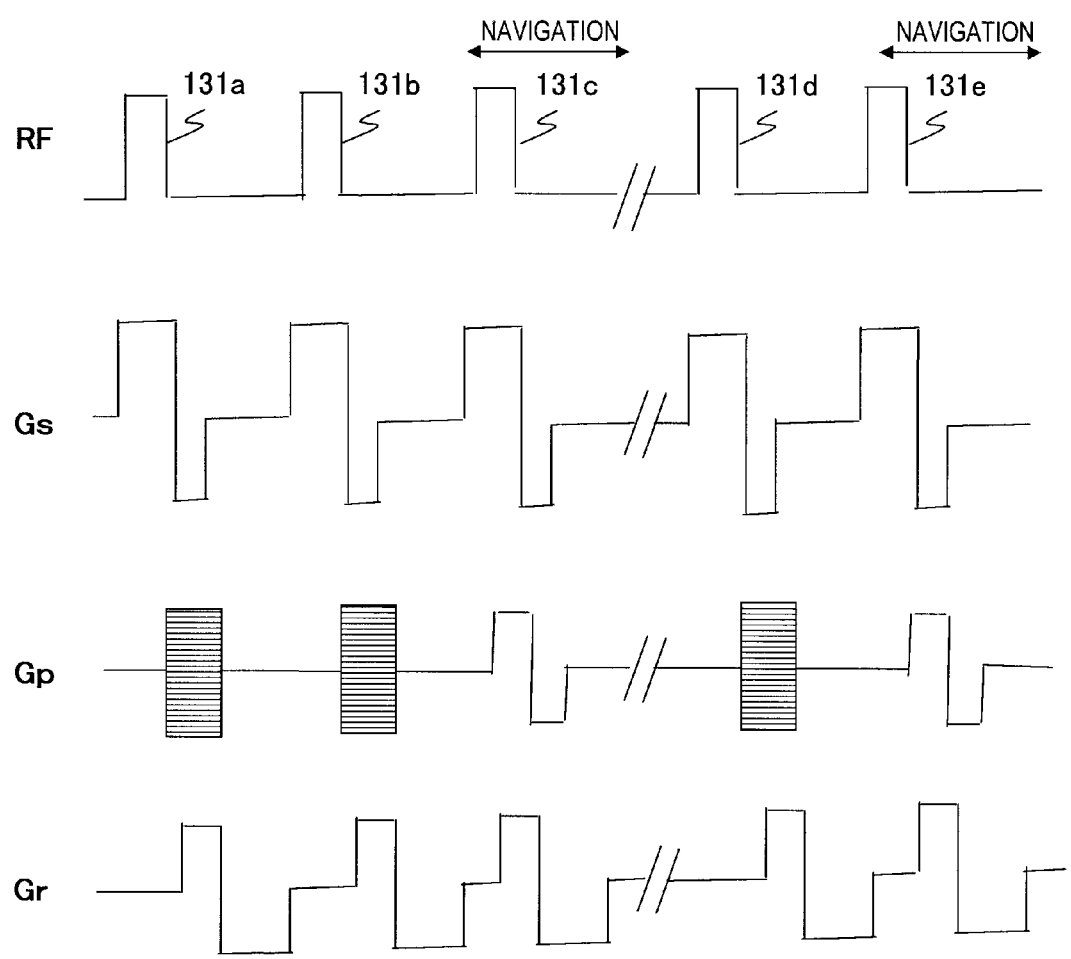

FIG. 13 explains the case, in a part of normal imaging sequence, of obtaining an echo by flow encoding instead of phase encoding for image acquisition, and using the obtained echo for detecting the table translation velocity.

FIG. 14 is an explanatory diagram of the MRI apparatus in embodiment 4.

BEST MODE FOR CARRYING OUT THE INVENTION

Figure 1:
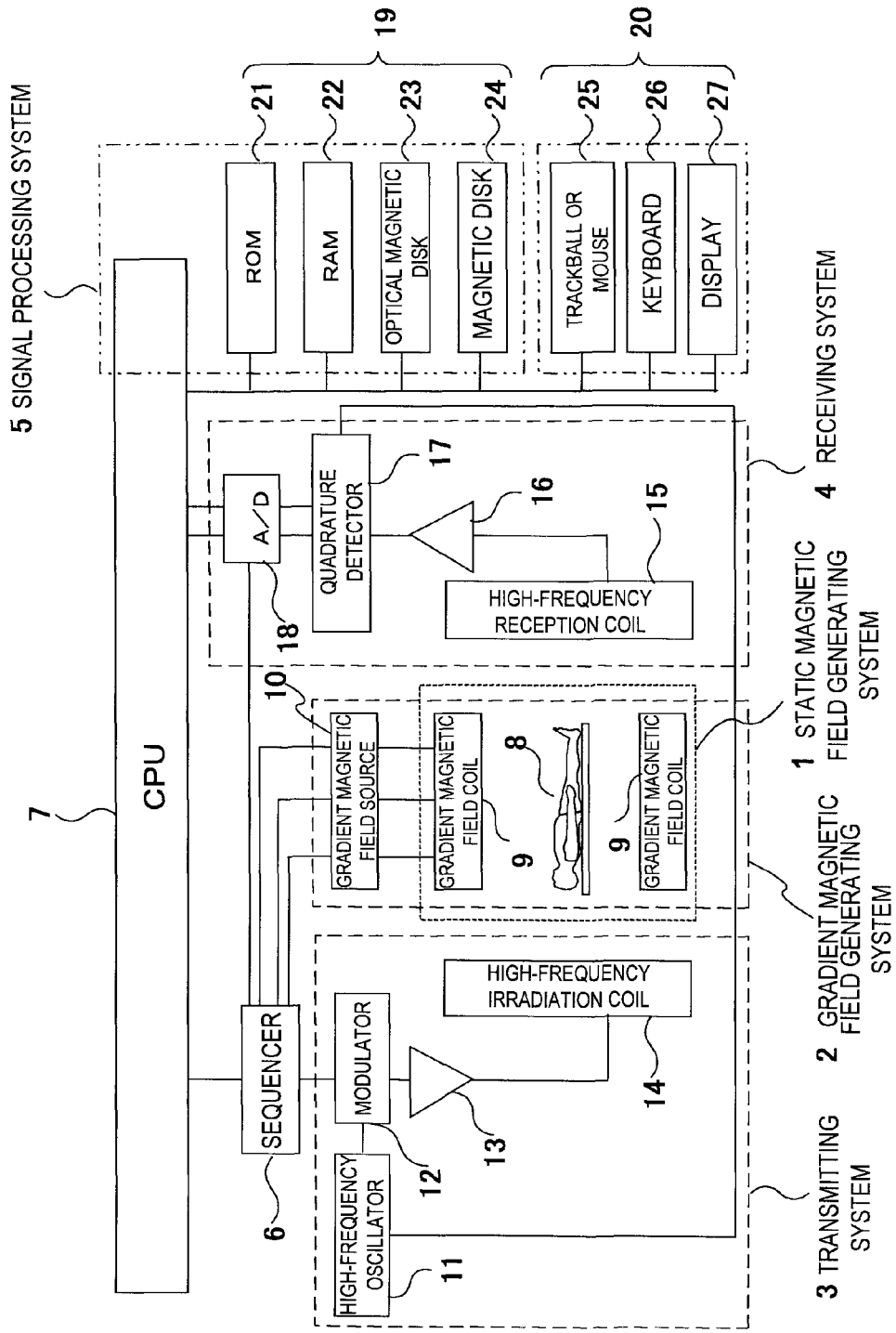
FIG. 1 is a block diagram showing the general configuration of an MRI apparatus related to the present invention.

FIG. 1 is a block diagram showing the general configuration of the MRI apparatus related to the present invention. As shown in FIG. 1, the MRI apparatus mainly comprises a static magnetic field generating system 1, a gradient magnetic field generating system 2, a transmitting system 3, a receiving system 4, a signal processing system 5 and a control system (a sequencer 6 and a CPU 7).

The static magnetic field generating system 1 is for generating a homogeneous static magnetic field in a space around an object 8 (imaging space), and is formed by a magnetic device using the permanent magnet method, normal conduction method or superconduction method.

The gradient magnetic field system 2, when the direction of the static magnetic field is set as Z-direction and the two directions orthogonal to the Z-direction is set as X-direction and Y-direction, is formed by three gradient magnetic field coils 9 for generating a gradient magnetic field pulse in the previously mentioned three axis directions, and a gradient magnetic field source 10 for driving those coils respectively. By driving the gradient magnetic field source 10, the gradient magnetic field pulse can be generated in three axis directions of X, Y and Z-axes or the direction in which these directions are combined. The gradient magnetic field pulse is applied so as to specify the imaging position in the object 8 and to impart positional information to the NMR signal generated from the object 8.

The transmitting system 3 comprises a high-frequency oscillator 11, a modulator 12, a high-frequency amplifier 13 and a high-frequency irradiation coil 14 for transmission. After an RF pulse generated by the high-frequency oscillator is modulated by the modulator 12 into a signal of a predetermined envelope, an electromagnetic wave for causing an atomic nuclei of an atomy by which the object is formed to generate nuclear magnetic resonance (high-frequency signal, RF pulse) is irradiated to the object by amplifying the modulated signal by the high-frequency amplifier 13 and applying it to the high-frequency irradiation coil 14. The high-frequency irradiation coil 14 is normally placed in the vicinity of the object.

The receiving system 4 comprises a high-frequency receiving coil 15 for reception, an amplifier 16, a quadrature detector 17 and an A/D converter 18. The NMR signal generated from the object as a response to the RF pulse irradiated from the high-frequency irradiation coil 14 for transmission is detected by the high-frequency receiving coil 15 for reception, amplified by the amplifier 16, converted into digital quantity by the A/D converter 18 via the quadrature detector 17, and transmitted to the signal processing system 5 as biserial collected data.

The signal processing system 5 comprises a CPU 7, a memory device 19 and an operation unit 20, and performs a variety of signal processing such as Fourier transformation, calculation of correction coefficient and image reconstruction to the digital signal received by the receiving system 4 in the CPU 7. The memory device 19 comprises a ROM 21, RAM 22, an optical disk 23, a magnetic disk 24, etc., and stores respectively, for example, programs for performing image analysis processing and measurement over time and invariable parameters to be used for performing the program thereof to the ROM 21, measurement parameters acquired in the entire measurement and echo signals detected in the receiving system to the RAM 22, and the reconstructed image data to the optical disk 23 or the magnetic disk 24. The operation unit 20 comprises input means such as a trackball, a mouse 25 or a keyboard 26 and a display 27 for displaying GUI necessary for the input and the processing results in the signal processing system 5. Information necessary for each process or control to be performed by CPU 7 is inputted via the operation unit 20. Also, the acquired images are displayed on the display 27.

The control system comprises a sequencer 6 and a CPU 7, and controls operation of the above-described gradient magnetic field generating system 2, the transmitting system 3, the receiving system 4 and the signal processing system 5. Particularly, application timing of gradient magnetic field pulses and RF pulses that are generated by the gradient magnetic generating system 2 and the transmitting system 3 and acquisition timing of the echo signals by the receiving system 4 are controlled by pulse sequence determined in advance in accordance with the imaging method via sequencer 6.

Embodiment 1

Figure 2:
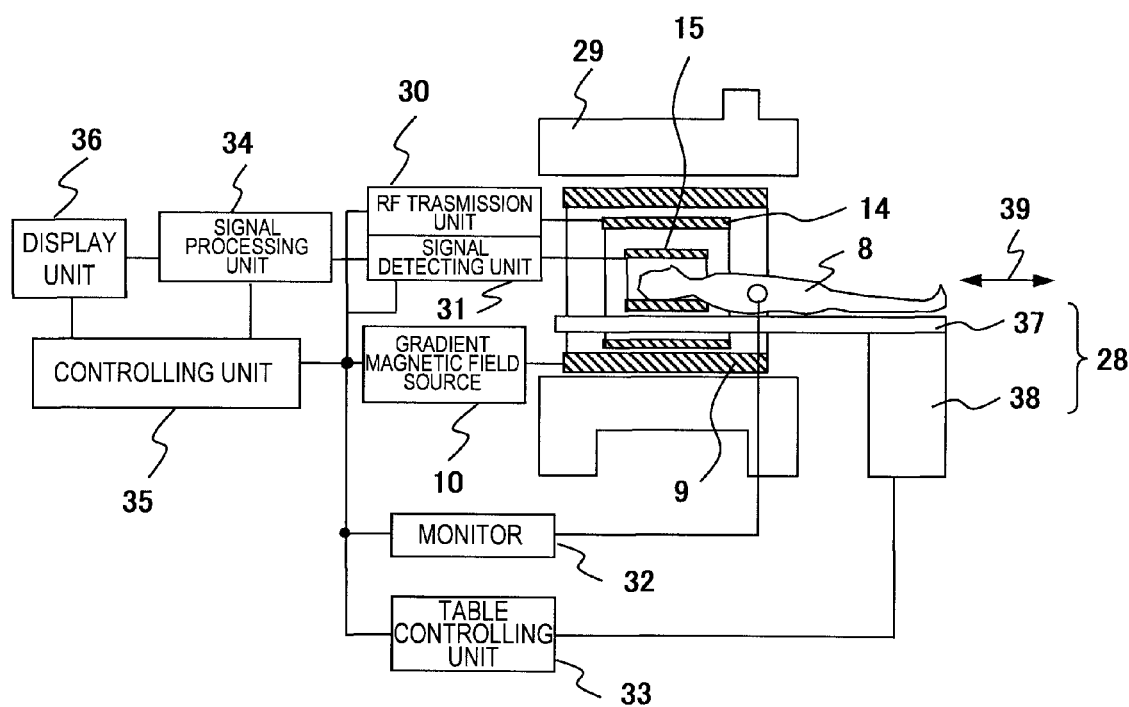
FIG. 2 shows a concrete configuration of the MRI apparatus in embodiment 1.

Next, the concrete configuration of the MRI apparatus in embodiment 1 will be described using FIG. 2. In FIG. 2, the MRI apparatus comprises a bed 28 on which the object 8 is placed, a magnet 29 for generating a static magnetic field around the object 8, a gradient magnetic field coil 9 for generating a gradient magnetic field in the imaging space of the static magnetic field space, a high-frequency (RF) irradiation coil 14 for generating a high-frequency magnetic, field in the imaging space, and a high-frequency reception coil (RF probe) 15 for detecting an NMR signal produced from the object 8. The MRI apparatus further comprises a gradient magnetic field source 10, an RF transmission unit 30, a signal detecting unit 31, a monitor 32, a bed control unit 33, a signal processing unit 34, a control unit 35 and a display unit 36.

The gradient magnetic field coil 9 comprises a gradient magnetic field coil in X, Y and Z-directions, and generates a gradient magnetic field in accordance with the signal from the gradient magnetic field source 10 respectively. The high-frequency irradiation coil 14 generates a high-frequency magnetic field in accordance with the signal from the RF transmitting unit 30. An output signal from the high-frequency receiving coil 15 is detected by the signal detecting unit 31, signal processed by the signal processing unit 34, and converted into an image signal by calculation. The image is displayed on display unit 36. The gradient magnetic field source 10, the RF transmitting unit 30 and the signal detecting unit 31 are controlled by the control unit 35. A time chart of control is generally referred to as the imaging pulse sequence. By this imaging pulse sequence, it is possible to image the configuration of the head region, abdominal region or four limbs of the body or the function of the blood vessel (lifeblood, blood flow) etc. two-dimensionally or three-dimensionally, for example, by setting protons which are the main constituent of the object 8 as an imaging target and imaging the spatial distribution of proton intensity or the spatial distribution of relaxation phenomena of the excitation state.

The bed 28 comprises a table 37 for the object to be laid, and a driving mechanism 38 of the table 37. The driving mechanism 38 moves the table 37 in head-foot (H-F) direction of the object 8 (an arrow 39 in FIG. 2) under the control of the bed control unit 33. The bed control unit 33 moves the position of the object 8 continuously while interfacing with the execution of the imaging pulse sequence under control of the control unit 35, which actualizes the moving-bed imaging method for imaging while continuously translating the object. Typical translation velocity of the table 37 is 0.5 cm/s~2.0 cm/s in head to feet direction. The monitor 32 is a device for monitoring heartbeat, pulse wave, electrocardiographic wave or respiratory movement of the object 8, converting the monitored biological information into electrical signals or optical signals, and transmitting the converted signals to the control unit 35 in real time.

Figure 3:
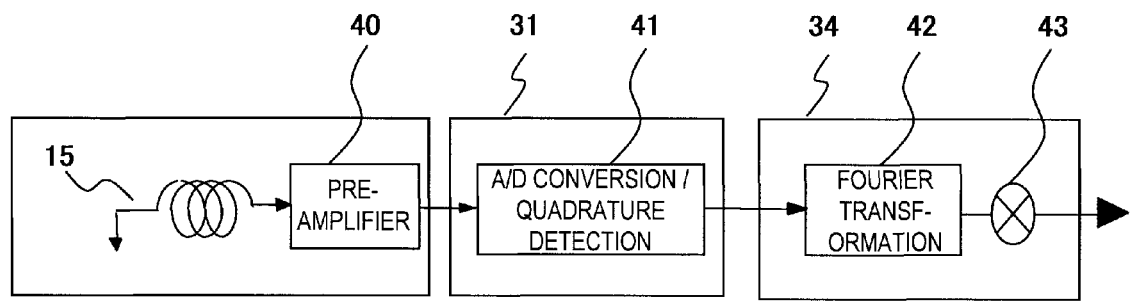
FIG. 3 shows a concrete example of a signal detecting system in embodiment 1.

Next, FIG. 3 shows a concrete example of the signal detecting system in embodiment 1. In FIG. 3, the high-frequency reception coil is indicated as 15. The pre-amplifier connected to the high-frequency reception coil 15 is indicated as 40 (indicated as 16 in FIG. 1). The A-D converter/quadrature detector circuit connected to the pre-amplifier 40 and mounted in the signal detecting unit 31 is indicated as 41 (indicated as 17 and 18 in FIG. 1). A Fourier transformation unit for acquiring an image by Fourier transformation which is connected to the output of the A-D converter/quadrature detector circuit 41 and mounted in the signal processing unit 34 is indicated as 42 (mounted in 5 or 7 in FIG. 1). A calculation unit which is mounted in the signal processing unit 34 and connected to the Fourier transformation unit 42 which performs posttreatment and synthesizing process on the previously acquired image is indicated as 43 (mounted in 5 or 7 in FIG. 1).

Next, detailed explanation of the present embodiment will be described using FIGS. 4 (*a*)~(*c*). First, FIG. 4 (*a*) is a schematic diagram of the apparatus configuration of the present embodiment viewing from the side of the object.

Figure 4:
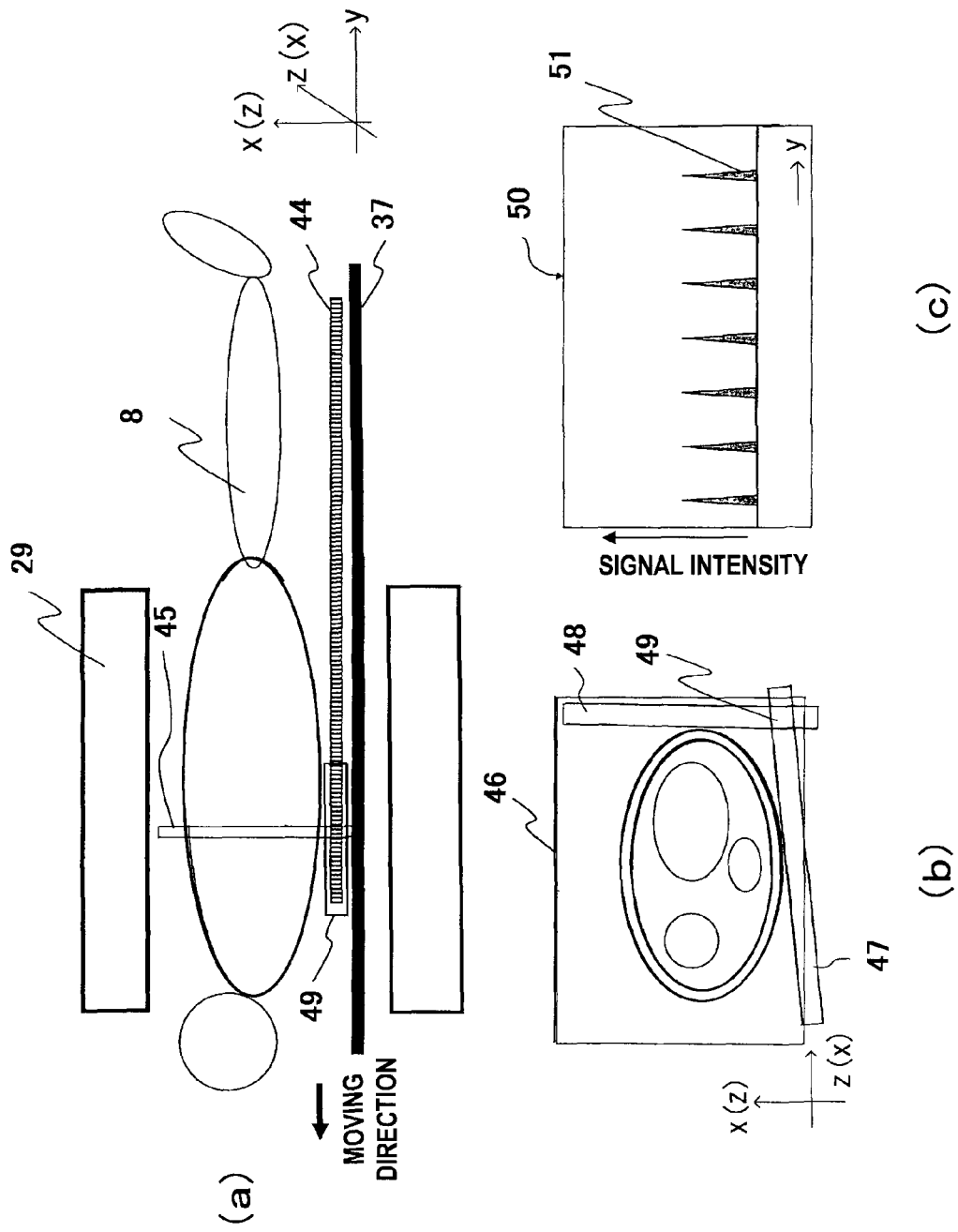
FIG. 4 is for explaining more details of embodiment 1.

According to FIG. 4 (*a*), in embodiment 1, a scale 44 is fixed on the table 37. A cross-section upon imaging the object by the imaging sequence to be described later is indicated as 45. The scale 44 has rectangular parallelepiped shape, and is placed so as to translate the table in the longitudinal direction thereof. The scale 44 is configured by a bar-like member (for example, 4 cm×4 cm×200 cm), formed by a non-magnetic material that generates NMR signals being incised with comb-like snicks at predetermined intervals along the longitudinal direction, or having configuration wherein the substance that emits intense resonance signals and the substance that emits weak resonance signals are alternately arranged. The interval of the teeth of the comb (or the interval between the material layers that emits intense NMR signals) is laid out in advance in accordance with the translation velocity of the table 37. The echo signal of the scale 44 is obtained from the navigator sequence wherein the table translation direction is the application direction of the readout gradient magnetic field, and the NMR signal intensity pattern representing the shape of the teeth of the comb of the scale 44 is obtained. The navigator echo sequence here is the one that obtains navigator echo from a region 49 wherein regions 47 and 48 are excited and overlapped on a cross-sectional image 46 in FIG. 4 (*b*). Also, by performing one-dimensional Fourier transformation on the obtained navigator echo in the longitudinal direction of the scale 44, the NMR signal intensity pattern in the direction thereof (one-dimensional profile) is obtained as shown in graph 50 in FIG. 4 (*c*). The one-dimensional profile 51 obtained on the graph 50 is corresponded to the shape of the substance that generates the NMR signals by which the scale 44 is formed, and has a shape of, for example, teeth of a comb shown in FIG. 4 (*c*). By detecting information such as the peak of the one-dimensional profile, the position of the scale 44 along with the position of the table on which the position of the scale is set can be recognized for each navigator sequence. In this regard, however, that the shape of a tooth of the comb has a pointed triangle shape in FIG. 4 (*c*) due to the loss of the edge by the partial volume effect, and it is considered that the signal becomes trapezoidal shape due to the same reason in the case that the width of a tooth of the comb is even wider.

The position that the scale 44 is attached to the table 37 is where the scale 44 does not stand in the way of imaging the object 8, which is the position that the scale 44 does not needlessly excite the object when the navigator sequence is executed for obtaining the echo of the scale 44. Thus it is desirable to attach the scale 44, for example, on either the right side or the left side of the table 37.

Figure 5:
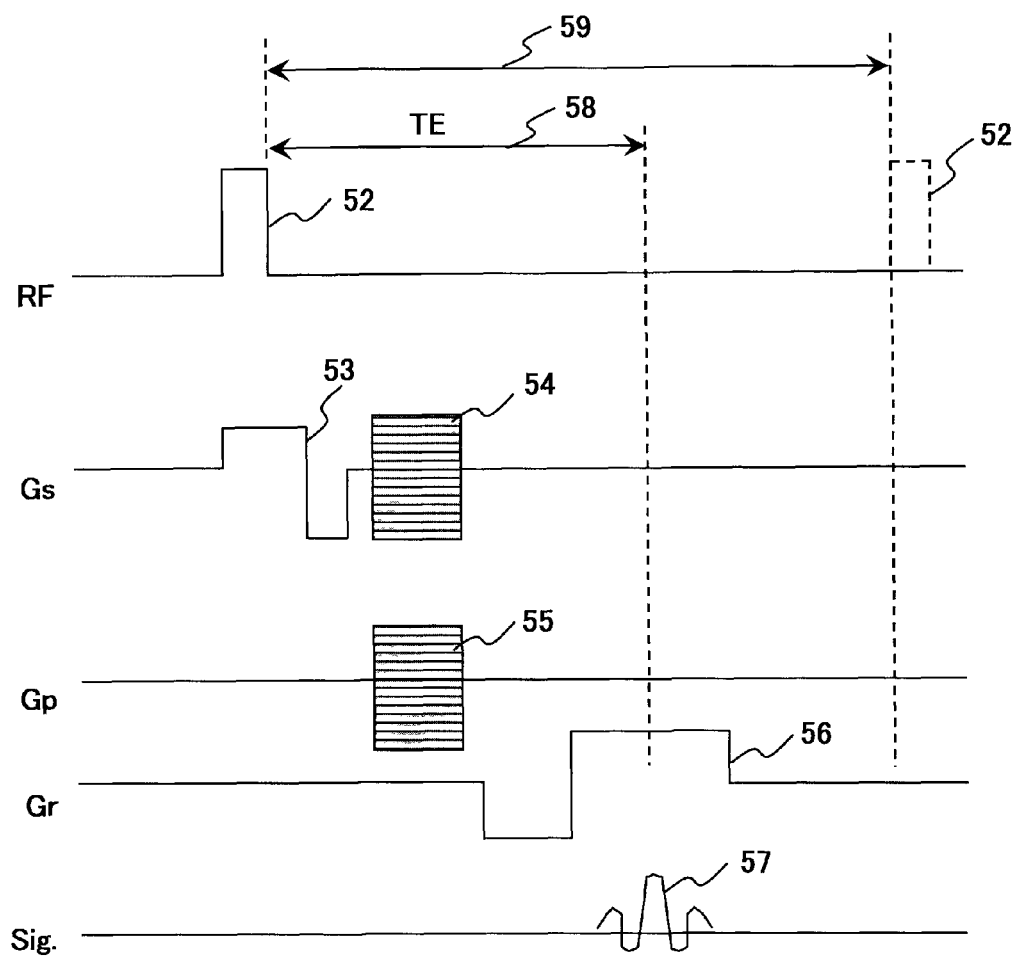
FIG. 5 shows a 3D gradient echo sequence that is an example of a typical imaging sequence for acquiring an image of an object.

Next, a commonly known 3-D gradient echo sequence will be described using FIG. 5, as an example of a typical imaging sequence for acquiring an image of the object. In the sequence in FIG. 5, a high-frequency pulse 52 irradiated by the high-frequency irradiation coil 14 and a slice-selecting gradient magnetic field pulse 53 generated by the gradient magnetic field coil 9 are applied at the same time, and the magnetization intensity of the predetermined slice (indicated as 45 in FIG. 4 (*a*)) is excited at a predetermined flip angle. Next, after a slice encode gradient magnetic field pulse 54 having a predetermined encode amount and a phase encode gradient magnetic field pulse 55 are applied, an echo signal 57 generated in the vicinity of an echo time TE is obtained by the high-frequency reception coil 15 while a readout gradient magnetic field pulse 56 is being applied. By repeating this sequence at repetition times (TR) 59, the echo signal necessary for reconstructing a piece of 3-D image is obtained. At this time, the amount of slice/phase encode gradient magnetic field pulse 54/55 is changed for each repetition time 59, and the different slice/phase encode is provided.

As for the number of the slice encode and the phase encode, combination of the values such as 32, 64, 128, 256 and 512 are normally selected for one piece of 3-D image. The respective echo signals are converted into, for example, a time series signal formed by 128, 256, 512 or 1024 of sampling data by the signal detecting unit 31. The signal processing unit 34 constructs a piece of 3-D MR image by performing 3-dimensional Fourier transformation on the time series signal. In FIG. 5, while a slice direction "s", a phase encode direction "p" and a readout direction "r" can be set in a predetermined direction, it is set here in either direction of the x, y or z-axis (y-axis: body-axis direction, x and z-axes: direction that are orthogonal to the y-axis respectively) shown in FIG. 4 (*a*).

Next, the navigator sequence by the MRI apparatus related to the present embodiment for obtaining an image of the object while recognizing the position of the table 37 by executing the navigator echo will be described. In the present imaging method, the navigator echo is obtained by executing the navigator sequence at a predetermined timing, and the position of the table during translation is continuously monitored. The execution timing of the navigator sequence is a predetermined timing such as an interval between the imaging pulse sequences for obtaining the image of the object (for example, after obtaining the necessary number of echo signals for reconstruction of a piece of image, every TR of the imaging pulse sequence (for example, 10 ms), or every predetermined number (for example, 10) of TRs (every segment).

A sequence diagram by a navigator sequence will be described using FIG. 6. In the navigator sequence, a navigator echo is obtained with respect to the prismatic navigator echo-obtaining region (indicated as 49 in FIG. 4 (*b*)) being set in advance so as to include a part of the scale 44 (3 cm×3 cm×2.5 m here) positioned in the imaging space. First, as shown in FIG. 6, by simultaneously applying a 90° RF pulse 61 and gradient magnetic field pulses 62 and 63 for slice-selection in x-direction by the high-frequency irradiation coil 14 and the gradient magnetic field coil 9, the magnetization intensity of the previously set first slice 47 shown in FIG. 4 (*b*) is excited by 90 degrees. Next, by simultaneously applying a 180° RF pulse 64 and gradient magnetic field pulses 65 and 66 for slice selection in x-direction and y-direction, the magnetization intensity of the previously set second slice 48 is excited by 180 degrees. Further, by applying gradient magnetic field pulses 67 and 68 for readout in y-direction, an echo signal 69 is generated from the prismatic region 49 where the first slice 47 and the second slice 48 are crossing, and is obtained by the high-frequency reception coil 15.

By performing one-dimensional Fourier transformation on the obtained echo signal 69 in y-axis direction (in longitudinal direction of the scale 44), the one-dimensional profile 51 is obtained as shown in the graph 50 of FIG. 4 (*c*). The obtained one-dimensional profile 51 shows the shape of the substance that generates the NMR signal by which the scale 44 is configured, that is the shape of the teeth of a comb here. By reading out the edge of this shape, the position of the table 37 in which the scale 44 is set can be recognized for each navigator echo signal on an intermittent basis.

Here, typical resolution of the profile data is about 256 points/256 mm. Therefore, positional resolution per data is 1 mm. In addition, by reading out the position of end of the edge or the pixel value of the end position from the graph 50 or performing easy data processing, it is possible to increase the resolution up to ⅟₁₀. Therefore, a typical positional accuracy of the position monitoring method by the scale 44 related to the present embodiment is 0.1 mm.

On the other hand, since the translation velocity of the table 37 is typically about 0.5 cm/s~2.0 cm/s, when the translation velocity is set, for example, as 2 cm/s and the velocity fluctuation ratio is supposed as about 5%, in the case of obtaining the navigator echo for each second, the positional variation to be measured turns out to be 1 mm/s between the echoes. In the present embodiment, since the variation of the table position can be accurately detected by detecting with the resolution of ⅟₁₀ using the edge processing and by the position detecting accuracy of 0.1 mm, the measurement accuracy of the table position using the scale 44 of the present embodiment is sufficiently accurate for executing the moving-bed imaging method which continuously translates, the table 37.

While acquisition interval of the navigator echoes can be arbitrarily set such as after completion of pulse sequence, for every TR (for example, 10 ms), or for every predetermined number (for example, 10) of TR (for every segment), when considering the objective of detecting the velocity fluctuation (or positional variation) of the table 37, it will be sufficient to set the acquisition interval for every is (or 0.1 s~2 s). Since the time necessary for execution of the typical navigator sequence as mentioned above is about 20 ms, the degree of the imaging pulse sequence being prolonged by the navigator sequence is 2% (or 20%~1%) which is substantially negligible range which does not lead to the extension of imaging time.

As for the intervals between the teeth of a comb for the scale 44, by setting it longer than the translation distance of the table 37 between the navigator echoes, it is possible to prevent the generation of errors in calculation of the distance or velocity of translation the table 37 due to the blurred boundaries between the adjacent teeth of the comb. For example, if the translation distance of the table 37 per acquisition interval of the navigator echo is the same as the intervals between the teeth of the comb, the one-dimensional profile turns out to be the same despite of the translation of the table 37, thus such arrangement of intervals between the teeth of the comb should be avoided. In this regard, however, in the case that the confusion of the adjacent teeth of the comb can be prevented by varying the shape or width of the adjacent teeth, it is assumed that the translation distance of the table 37 can be accurately calculated even when the intervals between the teeth of the comb are made short.

For example, in the case that the scale 44 is configured so as to periodically vary the signal intensity (amplitude) of the acquired one-dimensional profile as shown in FIG. 7 (*a*), in the case that the scale 44 is configured so as to periodically vary the peak intervals of the signal intensity of the one-dimensional profile as shown in FIG. 7 (*b*), or in the case that the scale 44 is configured so as to periodically vary the peak width of the one dimensional profile as shown in FIG. (c), it is possible to arbitrarily set the intervals of the teeth of the comb shorter than the table translation velocity per 1 TR, since the adjacent peaks (teeth of the comb) can be distinguished by respectively detecting the amplitude, peak intervals and peak width. For example, a period of the variation of amplitude, peak interval and peak width in FIG. 7 (*a*)~(*c*) may be set at the same rate as the length of the navigator echo acquisition region 49 in y-axis direction (for example, 20 cm). In addition, as for the configuration example of the scale 44 wherein the signal intensity (amplitude) is periodically varied as shown in FIG. 7 (*a*), the configuration can be used wherein the length of the tooth of the comb is periodically varied, or wherein the density of the substance which generates the NMR signal is periodically varied for every tooth of the comb. As for the configuration of the scale 44 wherein the peak interval is periodically varied as shown in FIG. 7 (*b*), the configuration can be used wherein the interval between the teeth of the comb (y-axis direction) is periodically varied. As for the configuration of the scale 44 wherein the peak width is periodically varied as shown in FIG. 7 (*c*), the configuration can be used wherein the thickness of the comb in y-axis direction is periodically varied.

Also, since the above-mentioned navigator sequence for monitoring the scale 44 irradiates a 90° RF pulse 61 and 180° RF pulse 64, when the navigator sequence is executed right before the imaging sequence, the signal intensity of an echo signal 57 acquired in imaging sequence declines in the region of irradiation slices 47 and 48 in FIG. 4 (*b*). Consequently, if the slices 47 and 48 and the part of the object 9 in the cross-sectional image 46 of FIG. 4 (*b*) are overlapped, dark band artifacts are generated there. Given this factor, as shown in the image display example 46 of FIG. 4 (*b*), the slice 47 and 48 should be displaced from the position of the object, and the navigator echo acquisition region 49 of the scale 44 should be placed at the position being displaced from the object 8. By doing so, it is possible to obtain echo data from the region 49 by irradiating the RF pulse in the navigator sequence to the slices 47 and 48 without influencing the cross-sectional image of the object 8.

FIG. 8 shows an example of the relationship between the position of the table 37 obtained by the navigator echo of the above-mentioned present embodiment and the table position in the case without any error in table translation, which is represented in a graph form of the apparatus coordinate system. In the example of FIG. 8, while the set value of the table translation velocity stays constant temporally and the table position is supposed to be varied in a straight line as shown in graph 81, it can be recognized that the actual measurement of the table position by the navigator echo varies stepwise and the fluctuation is generated in the velocity, for example, as shown in graph 82, due to factors such as the current fluctuation of the motor which drives the table 37. On the other hand, when the graph 82 is expressed in the translation coordinate system of the table in the case without any errors in the velocity or position of the table, it turns out as shown in graph 83. By this factor we learn that the position to be actually imaged has deflection influenced by factors such as current fluctuation of the motor by the velocity error or positional error of the table. In this regard, however, the graphs 84 and 85 in FIG. 8 illustrate that the imaging sequence and the navigator sequence are alternately executed.

In this embodiment, calculation of the positional error or velocity error of the table shown in FIG. 8 will be concretely carried out by the following methods. The first method stores in advance to a storage device in what timings the position of the teeth of the comb of the scale being fixed to a predetermined position of the table are obtained as a one-dimensional profile in the case that the table is accurately translated to the set position. Then the difference between the positions and the timings in the stored one-dimensional profile, and the positions and timings detected by the actually obtained one-dimensional profile is to be acquired. In the second method, in the case of imaging the whole body of the object using the moving table imaging method or multi-station imaging method while moving the imaging range from the head region to the foot region of the object, a part of the one-dimensional profile of the scale in the head region is stored in advance, and based on the stored profile, the measurement of the one-dimensional profile of the scale in the abdomen region or foot region being in the downstream in the case that the table translation is accurate is estimated. Then based on the difference between the positions of the teeth of the comb of the estimated one-dimensional profile and the actual positions of the teeth of the comb, the positional error or the velocity error is to be calculated.

In the present embodiment, the position and the velocity of the table can be measured in real time by detecting the navigator echoes using the above-described MRI apparatus and the method thereof, and in the case that positional displacement or fluctuation of velocity from the originally set position or velocity, the present embodiment immediately takes the correction measures of the feed back or feed forward to the front end system (measurement control system) of the MRI apparatus. For example, as for the first correction method, in the imaging sequence right after acquiring the navigator echo, the slice to be originally excited is excited by adjusting the frequency or phase of the RF excitation pulse in consideration of the displacement quantify of the table 37. By doing so, displacement of the exciting slice due to the displacement of the table 37 can be corrected. As for the second correction method, though the echo signal is obtained using the imaging sequence without any processing even when the table 37 is displaced, the position of the readout direction or the phase encode direction can be corrected by adding the specific offset to the reference frequency upon the echo signal acquisition or the specific phase to the acquired signal. By this method, displacement can be corrected by the correction process of the signal upon or after the acquisition. Compared to the first correction method, the second method does not need to change the frequency or phase of the RF excitation pulse of the imaging pulse sequence in the middle of the imaging sequence, and has the advantage that the positional displacement can be corrected by processing the signal upon or after its acquisition. The third correction method is, in the case that the position of the table 37 is displaced, to perform feedback control on the bed control unit 33 and correct the position of the table 37 so that any more positional errors of the table will not be generated.

The above-described three correction methods have the advantage that the correction means can be easily mounted since the measurement and processing of the positional fluctuation can be performed in the MRI front-end system, and the result thereof can be utilized immediately after the measurement and processing to correct the fluctuation of the position and velocity in real time. In this regard, however that the factors such as the kind of imaging sequence to be executed upon imaging the object need to be taken into consideration as for choosing the correction method for correcting the positional fluctuation from the above-described three methods. For example, the second method that changes the reference frequency is a technique considered useful for the table translation in the direction of the readout gradient magnetic field in the imaging sequence. Also, as for the method to add a specific phase, in the case that the table is displaced in the direction of the slice encode or phase encode, the specific phase should be added to correct the displacement due to the shifting of the phase of the entire echo for the portion of the time integral of the error generated in the rotation frequency during the application of the magnetic field caused by the intensity of the slice encode gradient magnetic field (or the phase encode gradient magnetic field) being too strong or too weak. In this way, it is needless to say that attention needs to be paid on properly choosing which correction method should be used in accordance with the kind of imaging sequence to be executed.

The difference in the navigator echo of the present embodiment from the conventional navigator echo is that it detects the table translation velocity, not the movement of a human body. Also, one of the techniques by the conventional navigator echoes is a technique for gating to select the range of the acquired echo data for image reconstruction according to the detected positions of a diaphragm. On the other hand, the method of the present embodiment executes correction using several methods by detecting the positional and velocity errors of the table translation, thus is different from the conventional method for detecting the movement (respiratory motion, etc.) of a human body.

While the example for fixing only one kind of scale 44 to the table 37 is described in the above-mentioned embodiment, it is possible to configure the scale 44 to be mounted in table 37 as an exchangeable type. By such configuration, for example, it may be mounted in the table 37 by preparing in advance a plurality of scales 44 having different intervals between the teeth of a comb or a plurality of scales 44 that are different kinds as shown in FIGS. 7 (*a*)~(*c*) and enabling an operator to select the most suitable scale 44 according to the kind of imaging pulse sequence or the table translation velocity. Here, the method for selecting the most suitable scale according to the kind of sequence means, for example, in the case of collecting navigator echoes for every 1 TR when the table translation velocity is constant and TR of the sequence is different, to use the scale having the long intervals between the teeth of the comb when the TR is long, and to use the scale having short intervals between the teeth of a comb when the TR is short. It is also possible to fix the plurality of scales 44 in advance to different parts of the table 37 (for example, the right side and the left side of the object laid down on the back). By doing so, the scale can be selected without exchanging, by choosing the most suitable scale 44 and setting the navigator echo acquiring region 49 at the position of the selected scale, in accordance with the kind of imaging pulse sequences or the table translation velocity.

Also, while the scale 44 is arranged parallel to the moving direction of the table 37 (y-axis direction) in the above-embodiment, the direction for arranging the scale 44 (longitudinal direction of the scale 44) does not necessarily have to be parallel to the translating direction of the table (y-axis direction). For example, through arranging the scale parallel to the x-axis direction as shown in 91a~f in FIG. 9 (a) having predetermined intervals in the translation direction of the table 37 (y-axis direction), it is possible to detect positional accuracy of the table in the x-axis direction. This technique is especially effective in the open-type MRI apparatus wherein a pair of magnets are arranged facing each other. Because in the case of, open-type MRI apparatus, there are occasions that the imaging and surgery are performed while moving the table not only in y-direction but also in x-direction as shown in FIG. 9 (b). In order to detect the table movement in x-axis direction by the scale arranged in x-axis direction, a sequence diagram such as the one shown in FIG. 9 (c) may be used. Here, the direction for applying a readout gradient magnetic field is the x-axis direction (Gx), and the region at which the scales 91a~f are arranged are included in the region in which the echo signals are collected upon the application. Also, in order to move the table of the open-type MRI apparatus shown in FIG. 9 (b) in vertical direction (z-direction) or to detect the positional accuracy or moving accuracy in the z-direction of the table, the navigator echo sequence can be executed which has the z-direction as the direction for applying the read-out gradient magnetic field direction, by arranging the scales so its longitudinal direction becomes the z-direction.

Also, while the case of continuously translating the table 37 is described in the above embodiment, the scale of the present embodiment can be used for the multi-station imaging method which performs imaging by dividing the target imaging region into a plurality of regions (stations) and stopping the table 37 at the respective stations, in order to detect the position at the respective stations.

Embodiment 2

The MRI apparatus of embodiment 2 related to the present invention will be described using FIGS. 10 (a), (b) and (c). The MRI apparatus of the embodiment 2 is configured similar as the embodiment 1 in obtaining an image of the object while recognizing the position of the table 37 by the navigator echo, but different in not using the scale fixed on the table and in using the structure of the object 8 as an index for recognizing the position.

First, FIG. 10 (a) shows the schematic view of the apparatus configuration in the present embodiment viewing from the side of the object. In accordance with FIG. 10 (a), a navigator echo acquisition region 101 is set in the inside of the object 8, and a navigator echo is obtained by the same navigator sequence as the embodiment 1. FIG. 10 (b) shows the cross-sectional image 102, and the navigator echo acquisition region 101 is placed inside of the object 8. The echo signal is A/D converted into a time-series signal by the signal detecting unit 31, and graph 103 as shown in FIG. 10 (c) is obtained by performing one-dimensional Fourier transformation by the signal processing unit 34 with respect to the y-axis direction (body-axis direction). The obtained one- dimensional profile 104 has the shape that reflects the configuration of the object 8. This profile shifts on an intermittent basis in y-axis direction in accordance with the translation of the table 37 in y-axis direction, and the profile obtained in the next navigator echo becomes, for example, as a one-dimensional profile 105 shown in FIG. 10 (c). Accordingly, by obtaining the shift amount between the profiles 104 and 105 in y-axis direction, the shifting distance of the table 37 in the elapsed time from the echo signal acquisition time of the profile 104 to the echo signal acquisition time of the profile 105 can be easily and accurately obtained by calculation.

In the case of obtaining the shift amount of the one-dimensional profiles represented by 104 and 105 more concretely, the shift amount can be easily obtained by calculating correlation of 104 and 105 while shifting both profiles. At this time, a characterizing point that appears on the one-dimensional profile can be set as an index for calculating the shift amount. For example, position of the parietal region can be set as an index for calculating the shift amount upon imaging a head region, the diaphragm can be set as an index upon imaging a chest region, and vertebral bone can be set as an index upon imaging a spine. Also, in four limbs, the edge that can be obtained in a knee joint or elbow joint can be set as an index. Also, the movement error of the table may be obtained by imaging a scanogram to be used for positioning the object in advance, recognizing and storing the correlational positional relationship between the characterizing portions of the object on the basis of the scanogram, and obtaining the degree of difference between the characterizing region on the one-dimensional profile obtained upon the actual translation of the table and the characterizing region when the table translation is accurate, on the basis of the stored correlational positional relationship.

The explanation other than that the region 101 is set inside of the object 8 will be omitted since it is the same as the embodiment 1.

In the embodiment 2, while the navigator echo can be obtained to monitor the position or velocity of the table by navigator sequence, it is also possible to use the signal obtained in the imaging sequence for monitoring the position or velocity of the table. For example, in the imaging sequence shown in FIG. 5, by setting the direction of the readout gradient magnetic field 56 so as to be consistent with the translation direction (y-axis direction) of the table 37, the echo signal 57 obtained when the encode amount by the gradient magnetic field for phase encoding is zero can be used for monitoring the position or velocity of the table. By converting the obtained echo signal into the time-series signal by the signal detecting unit 31 and performing the one-dimensional Fourier transformation with respect to the y-direction (body-axis direction) by the signal processing unit 34, the one-dimensional profiles as shown in 104 and 105 of FIG. 10 (c) can be obtained. In this case, since the profile reflecting the configuration of the object 8 can be obtained without executing the navigator sequence, table translation distance can be obtained without extending the imaging time for executing the navigator sequence.

Embodiment 3

The MRI apparatus of the embodiment 3 related to the present invention will be described using FIGS. 11 (a)~(c) and FIG. 12. Embodiment 3 has the same configuration as the embodiment 1 in obtaining an image of an object while monitoring the position of the table 37 by the navigator echo, but is different in that it continuously monitors the table translation position using the phase contrast (PC) method in the navigator sequence.

First, FIG. 11 (a) shows a schematic view of the apparatus configuration in the present embodiment viewing from the side of an object being laid on the table. As shown in FIG. 11 (a), the scale 111 configured by a substance that generates NMR signals is mounted on the table 37. The scale in the embodiment 3, however, has a prismatic shape homogeneous in longitudinal direction, not the comb shape as in the embodiment 1. In this embodiment, the translation distance of the table 37 is measured by obtaining the echo signal with respect to the scale 111 by one-dimensional PC sequence (hereinafter referred to as a navigator PC echo) as shown in FIG. 12. The acquisition region of the navigator PC echo is set so as to include a scale 113 as shown in 111 of a cross-sectional image 112 in FIG. 11 (*b*).

FIG. 12 is a sequence diagram in the present embodiment. Though FIG. 12 is similar to the navigator sequence in FIG. 6 described in the embodiment 1, it is different from the navigator sequence in FIG. 5 in that a negative gradient magnetic field pulse 121*a* and a positive gradient magnetic field pulse 121*b* are added to a readout gradient magnetic field in y-axis direction as a velocity encode pulse (one-dimensional dephasing pulse) 121. The positive gradient magnetic field pulse 121*a* and the negative gradient magnetic field pulse 121*b* are set so as to have the equal absolute value of multi-plication of the intensity of the gradient magnetic field pulse by the application time. In other words, in the case that the target substance is in resting condition, the phase rotation amount in the y-axis direction of the magnetization generated in the scale 121 by the negative gradient magnetic field pulse 121*a* and the phase rotation amount generated in the scale 121 by the positive gradient magnetic field pulse 121*b* has opposite directions and the same sizes.

In the case that the scale 121 is in resting condition, the phase of the echo signal 122 to be obtained in the y-axis direction is zero, since the appended phase rotation amount by the positive and the negative gradient magnetic field pulses 121 negate each other. However, when the scale 111 is moved to the y-axis direction due to the movement of the table 37, the phase is not zero since the phase rotation amount generated in the positive and negative gradient magnetic field pulses 121 are different and the phase components in the y-axis direction of the echo signal to be detected do not negate each other. Also, the phase rotation amount of the echo signal is in proportion to the velocity of the table 37. Accordingly, the table velocity can be measured by detecting the phase rotation amount in the y-direction of the detected echo signal by the navigator PC echo, and the table translation error can be detected and used for correction by calculating the difference between the measured value and the preset value.

The phase rotation amount in the y-axis direction of the navigator PC echo can be detected by the signal processing unit 34. The detected phase rotation amount turns out, for example, as shown in graph 114 in FIG. 11 (*c*). The vertical axis is the phase rotation amount, and is in proportion to the table translation velocity. The lateral axis is the y-axis direction position, and the scale 113 turns out as a flat profile since it has one velocity as a whole. In the case that the phase rotation amount detected from the navigator PC echo which is executed later indicates the increment from 115 to 116 overtime as shown in the graph 114, the variation (increment) of the velocity at that time can be detected. Here, the movement velocity of the table to be detected is normally about 1~5 cm/s. Flow encode of the PC sequence is determined by setting this velocity as an index. For example, in the case of detecting the movement velocity of the table by setting the movement velocity as "v" by the phase amount being φ (φ<180°), the gradient magnetic field of the flow encode should be applied which satisfies the gradient magnetic field intensity "G" and the gradient magnetic field application time "t" expressed in the following formula.

$$\phi = \int \omega dt = \int (\gamma G v t) dt = \frac{1}{2} \gamma G v t \quad \text{[Formula 1]}$$

ω: angular frequency
γ: magnetic rotation number
G: gradient magnetic field intensity
v: table translation velocity
t: application time of the positive and negative gradient magnetic field In formula 1, "ω" indicates the angular frequencies, "γ" indicates the magnetic rotation number, "G" indicates the gradient magnetic field intensity, "v" indicates the table translation velocity, and "t" indicates the application time of the positive and negative gradient magnetic field.

In addition, on the tomographic image obtained in imaging sequence, for example, a cross section of the scale 111 is displayed on the lower right of the image along with the cross-section of the object 8 as shown in a cross-section 112 of FIG. 11(*b*).

While the navigator PC echo is obtained in the embodiment 3 by the sequence of FIG. 12, the echo may be obtained by executing the flow encoding instead of appending the phase encode for the image acquisition in a part of the usual imaging sequence to be used for detecting the translation velocity of the table. For example, FIG. 13 is a diagram of such a sequence. More specifically, FIG. 13 is an example of executing a sequence while applying five RF irradiation pulses 131*a*~*e* starting from the left. The first, second and fourth sequence from the left obtain the echo signal for constructing the magnetic resonance image by applying the phase encode gradient magnetic field for magnetic resonance field imaging. In the third and the fifth sequence from the left, instead of the phase encode gradient magnetic field, the gradient magnetic field for the phase contrast (PC) method, that is the two gradient magnetic field pulses having different polar characters of positive and negative and the same absolute value in multiplication of the intensity by the application time are applied. The example in FIG. 13 has an advantage that the navigator PC echo can be incorporated only by somewhat changing the application method of a gradient magnetic field in phase encode direction in between times of the usual imaging sequences.

Embodiment 4

The MRI apparatus in embodiment 4 of the present invention will be described using FIGS. 14 (*a*)~(*c*).

The embodiment 4 is similar as the embodiment 3 having the configuration in continuously monitoring the table translation position using the phase contrast (PC) method, but different in using the configuration of the object 8 itself for monitoring the phase amount instead of the scale. More specifically, it is for measuring the phase quantity of the region without movement such as breathing or heartbeat in the body of the object such as brain parenchyma or skeletal muscles, and obtaining the table translation velocity from the result of the measurement.

First, FIG. 14 (*a*) is a schematic diagram of the apparatus configuration in the present embodiment, viewing from the side of the object. In the present embodiment, the navigator PC echo is to be obtained from the sequence in FIG. 12 by setting the navigator PC echo acquisition region 141 in the object 8 as shown in FIG. 14 (*a*). A cross-sectional image 142 is shown in FIG. 14 (*b*), and the navigator echo acquisition region 141 is placed inside of the object 8. The profile of the phase amount acquired by the navigator PC echo turns out as 144 in graph 143 of FIG. 14 (*c*). The vertical axis indicates the phase amount (that is the velocity of the substance by which a part of the object is constituted), and is the same as the translation velocity of the table 37 in a part of the object without movement. The lateral axis indicates the position in the y-axis direction. In the case of actually using the living body as the object, the phase amount denoted in the profile 144 (velocity) is not necessarily flat due to the movement of the organ such as blood flow in the blood vessel or respiration to be added to the table translation velocity to be measured. However, if the profile of the phase amount acquired by the navigator PC echo measured after a predetermined time is the same as the graph 145, the fact that the fluctuation of the velocity (shift in the vertical direction) along with the fluctuation of the position (shift in the lateral direction) generated between the two navigator PC echoes can be detected. The shift amount in the vertical direction can be obtained by setting the value of the region without movement as an index. Or, for example, the velocity variation can be easily detected also by obtaining the average amount (value 144*a*, value 145*a*) of the phase amount (velocity) for each measurement by the signal processing unit 34, and measuring the difference between them. In the present embodiment, the movement error of the table 37 can be measured by the navigator PC echo without using the scale, and utilized for the correction.

In the cross-sectional image acquired by the imaging sequence, for example, only the cross-sectional image of the object 8 is displayed as shown in the cross-sectional image 142 of FIG. 14 (*b*), and the cross-section of the scale is not displayed. Also in embodiment 4, as in the same manner as embodiment 3 shown in FIG. 13, the echo can be obtained by flow encoding instead of appending the phase encode for image acquisition in the usual imaging sequence, and using the obtained echo for detecting the table translation velocity.

The present invention does not have to be limited to the above-described embodiments, and various changes may be made without departing from the scope of the invention. For example, while the position or velocity of the table are measured using the magnetic resonance signal detected by the navigator sequence or the navigator PC echo sequence, the present invention does not have to be limited to this method. The position or velocity of the table may be measured also by, for example, using an encoder. However, the apparatus for the method using the encoder is complex and expensive, the above-mentioned method using the magnetic resonance signal has an advantage of providing the apparatus at a moderate price. Also, while the apparatus by the method using the encoder requires two control means (CPU, etc.) for controlling the pulse sequence and controlling the encoder, the method by the magnetic resonance signal described in the above embodiments has a merit that the mounting of the computer can be simplified since the same control means can be used for both the pulse sequence control and the encoder control. Further, while the method using the encoder has a problem that the encoder itself might be an unnecessary noise source, the method using the magnetic resonance signal has an advantage that there is no risk of generating an unnecessary noise source.

Also, the present invention is not limited to the method for correcting the displacement of the position or velocity of the table acquired by the navigator echo indicated in the above-described embodiments that are the method for adjusting the frequency or phase of the irradiating RF exciting pulse (the first method), the method for adding an offset to the reference frequency or adding a specific phase to the obtained signal upon detecting the magnetic resonance signal detected by the high-frequency reception coil 15 (the second method), and the method for feeding back the displacement generated in the position or velocity of the table to the bed controlling unit 33 (the third method). For example, upon performing the Fourier transformation on the magnetic resonance signal obtained for imaging and arranging it in the hybrid space, the method may be used for displacing the position for arranging the signal considering the influence by the displacement of the table position or velocity.

Also, while the spin echo method for applying a 90° pulse and 180° pulse first in the navigator sequence or the navigator PC sequence in the above-described embodiments, it is possible to use the 2-dimensional selection excitation method by gradient echo method.

Also, while only the case for detecting displacement of the position or velocity of the table using one scale for one imaging is described in the above-described embodiments, the problem of the adjacent teeth of a comb being mixed-up and detected as one can be avoided by using a method such as using two scales arranged at the same time in one imaging (they may be either parallel or vertical).

Also, the present invention does not have to be limited to the example illustrated in the above-described embodiments 3 and 4 for applying the positive and negative gradient magnetic field pulses having the same absolute value of multiplication of the intensity by the application time of the gradient magnetic field pulse, for detecting the table translation velocity in the navigator PC sequence. For example, it is possible to detect the translation velocity of the table so as to construct a diffusion-weighted image by applying the positive and negative gradient magnetic field pulses having the same absolute value of the multiplication of the intensity by the application time, in the same direction interleaving the 180° pulse in between.

Also, it goes without saying that the shape of the above-described scale does not have to be a rectangular parallelepiped.

The invention claimed is:

1. A magnetic resonance imaging apparatus comprising:
object placing means for placing an object to be examined in an imaging space;
translating means for translating the object placing means on which the object is placed in a given direction continuously or step-wise;
magnetic field generating means which is to be placed around the imaging space, and exciting the desired position of the object by generating a static magnetic field, gradient magnetic field and a high-frequency magnetic field in the imaging space;
signal detecting means to be placed around the imaging space, and for detecting a magnetic resonance signal generated from the object;
signal processing means for performing signal processing on the magnetic resonance signal detected by the signal detecting means, and constructing a magnetic resonance image of the object; and
control means for controlling the translating means, the magnetic field generating means, the signal detecting means and the signal processing means, so as to obtain a magnetic resonance image of the object while translating the object continuously or step-wise to a predetermined position at predetermined speed, characterized in further comprising:
    translation error detecting means for detecting an error of the position or the set value of the speed; and
    correcting means for correcting the error detected by the translation error detecting means.

2. The magnetic resonance imaging apparatus according to claim 1, wherein the translation error detecting means detects the error based on the magnetic resonance signal detected by the signal detecting means.

3. The magnetic resonance imaging apparatus according to claim 2, wherein:
    the object placing means comprises at least one object placing means positional information emitting means for emitting a magnetic resonance signal having the positional information of the object placing means; and
    the translation error detecting means detects the error based on the magnetic resonance signal generated from the object placing means positional information emitting means.

4. The magnetic resonance imaging apparatus according to claim 3, wherein:
    the object placing means positional information emitting means is formed by a scale that generates the magnetic resonance signal in a predetermined one-dimensional special intensity pattern; and
    the translation error detecting means comprises monitoring means for monitoring the position of the spatial intensity pattern based on the data by which the magnetic resonance signal is one-dimensionally Fourier transformed, and calculating means for obtaining the difference from the set value based on the position monitored by the monitoring means and calculating the error of the position or velocity of the object placing means.

5. The magnetic resonance imaging apparatus according to claim 4, wherein the scale is formed by a substance which emits an intense magnetic resonance signal and a substance which emits a weak nuclear magnetic resonance signal or does not emit the nuclear magnetic resonance signal, being arranged alternately in one-dimensional direction at predetermined intervals.

6. The magnetic resonance imaging apparatus according to claim 4, wherein the translation error detecting means detects a plurality of magnetic resonance signals at predetermined time intervals, obtains the position of the object placing means based on the position of a predetermined one-dimensional spatial intensity pattern of the scale acquired by the respective magnetic resonance signals, and detects the error based on the difference between the obtained position thereof and the set value of the position.

7. The magnetic resonance imaging apparatus according to claim 3, wherein the object placing means positional information emitting means is formed by a uniform substance which spatially generates the magnetic resonance signal in uniform intensity.

8. The magnetic resonance imaging apparatus according to claim 7, wherein:
    the control means comprises means for executing a navigator PC sequence which is a navigator sequence for generating and detecting a magnetic resonance signal using the translation error detecting means appended with a velocity encode pulse, and in the navigator sequence executed by the control means, a first slice plane excited by a first high-frequency pulse and a second slice plane excited by a second high-frequency pulse intersect, and the region where the first slice plane and the second slice plane intersect is to be at the position where the object placing means positional information emitting means is mounted.

9. The magnetic resonance imaging apparatus according to claim 8, wherein:
    the velocity encode pulse to be added to the navigator sequence is formed by two gradient magnetic field pulses having the opposite polar characters and the same absolute values of multiplication of the intensity by the application time; and
    the direction of gradient of magnetic field by the two gradient magnetic field pulses is the translation direction of the object placing means.

10. The magnetic resonance imaging apparatus according to claim 8 characterized in comprising:
    means, based on the magnetic resonance signal acquired by the navigator echo appended with a velocity encode pulse, for obtaining the profile of the phase quantity of the acquired magnetic resonance signal; and
    means for detecting the velocity of the object placing means based on the size of the obtained quantity.

11. The magnetic resonance imaging apparatus according to claim 8 characterized in comprising:
    means, based on the magnetic resonance signal acquired by the navigator echo appended with a velocity encode pulse, for obtaining the profile of the phase quantity of the acquired magnetic resonance signal;
    means for obtaining a shift amount indicating how much the profile shifts in moving direction of the object placing means over time; and
    means for detecting the velocity of the object placing means based on the shift amount.

12. The magnetic resonance imaging apparatus according to claim 3, wherein:
    the control means comprises means for executing a navigator sequence for generating a magnetic resonance signal from the object placing means positional information emitting means to detect an error using the translation error detecting means, and in the navigator sequence executed by the control means, a first slice plane excited by a first high-frequency pulse and a second slice plane excited by a second high-frequency pulse intersect, and the region where the first slice plane and the second slice plane intersect is to be at which the object placing means positional information emitting means is mounted.

13. The magnetic resonance imaging apparatus according to claim 3, wherein the one or more object placing means positional information emitting means include means having rectangular parallelepiped shape whose longitudinal direction is parallel to the longitudinal direction of the object placing means.

14. The magnetic resonance imaging apparatus according to claim 3, wherein:
    the magnet field generating means are placed facing each other on the opposite sides of the imaging space;
    the object placing means capable of translating not only in the longitudinal direction thereof, but also in horizontal direction which is vertical to the longitudinal direction; and
    the one or more object placing means positional information emitting means have rectangular parallelepiped shape, and include means whose longitudinal direction is arranged not only in the longitudinal direction of the object placing means but also in the direction vertical and parallel to the longitudinal direction of the object placing means, or include means arranged vertical to the object placing means.

15. The magnetic resonance imaging apparatus according to claim 2, wherein the translation error detecting means detects the error based on the magnetic resonance signal generated from inside of the object.

16. The magnetic resonance imaging apparatus according to claim 15, wherein the translation error detecting means detects the error based on a magnetic resonance signal produced from inside of the object, comprising:
- means for obtaining a plurality of one-dimensional profiles, by performing Fourier transformation on the plurality of magnetic resonance signals acquired having predetermined intervals;
- means for calculating the shift amount which indicates how far the one-dimensional profile obtained corresponding to the plurality of magnetic resonance signals are shifted in translating direction of the object placing means over the predetermined time intervals; and
- means for detecting the error based on the calculated shift amount.

17. The magnetic resonance imaging apparatus according to claim 15, wherein:
the control means comprises means for executing and detecting a navigator sequence for generating a magnetic resonance signal from inside of an object to be examined using the translation error detecting means, and in the navigator sequence executed by the control means, a first slice plane excited by a first high-frequency pulse and a second slice plane excited by a second high-frequency pulse intersect, and the region where the first slice plane and the second slice plane intersect is to be in the interior portion of an object.

18. The magnetic resonance imaging apparatus according to claim 15, wherein:
the control means comprises means for executing a navigator PC sequence which is the navigator sequence for generating and detecting a magnetic resonance signal using the translation error detecting means appended with a velocity encode pulse, and in the navigator sequence executed by the control means, a first slice plane excited by a first high-frequency pulse and a second slice plane excited by a second high-frequency pulse intersect, and the region where the first slice plane and the second slice plane intersect is to be in the interior portion of the object.

19. The magnetic resonance imaging apparatus according to claim 1, wherein the correcting means corrects the error, upon adjusting the frequency or phase of the generated high-frequency magnetic field in order to correct the error or detecting a magnetic resonance signal using the signal detecting means, by adding an offset to a reference frequency or adding a specific phase to the detected magnetic resonance signal.

20. The magnetic resonance imaging apparatus according to claim 1, wherein the correcting means corrects the error by performing correction to the translation of the object placing means executed by the translating means.

* * * * *